United States Patent [19]

Hu et al.

[11] Patent Number: 5,734,691
[45] Date of Patent: Mar. 31, 1998

[54] DETECTOR Z-AXIS GAIN NON-UNIFORMITY CORRECTION IN A COMPUTED TOMOGRAPHY SYSTEM

[75] Inventors: Hui Hu, Waukesha; Guy M. Besson, Wauwalusa; Hui David He, Waukesha, all of Wis.

[73] Assignee: General Electric Company, Milwaukee, Wis.

[21] Appl. No.: 779,960

[22] Filed: Dec. 23, 1996

[51] Int. Cl.$^6$ ............................................ A61B 6/03
[52] U.S. Cl. ............................ 378/4; 378/19; 378/901
[58] Field of Search ............................ 378/4, 19, 901

[56] References Cited

U.S. PATENT DOCUMENTS 5,473,656 12/1995 Hsieh et al. ..................... 378/901 X
5,579,359 11/1996 Toth .................................. 378/901 X

*Primary Examiner*—David P. Porta
*Attorney, Agent, or Firm*—John S. Beulick; John H. Pilarski

[57] ABSTRACT

The present invention, in one form, corrects any error due to varying detector cell gains in the z-direction represented in data obtained by a scan in a CT system. The CT system includes an x-ray source which emits an x-ray beam from a focal spot, through a collimator aperture, and towards a detector having a plurality of detector cells. The geometry of the x-ray beam, the width of the collimator aperture and the focal spot size are used to determine the z-profile of the x-ray beam across the detector cells. Such z-profile is used to identify effective detector cell gains. The identified effective detector cell gains, rather than actual detector cell gains, are used to correct errors due to varying detector cell gains. Particularly, the identified effective detector cell gains are employed in a known correction algorithm to correct errors. A local average in an x-direction of actual detector cell gain z-profiles is used to determine a non-rectangular norm detector gain z-profile. In one form of the present invention, and after correcting the image data for beam-hardening, the data is passed through a highpass filter to remove any data representing relatively slow, or low frequency, changes. Next, the filtered data is clipped and view averaged to remove high frequency data contents due to the objects being imaged. A slope estimate is then created. Using the slope estimate, an error estimate is generated. The error estimate is then subtracted from the beam-hardened corrected data, for example. As a result, errors due to z-axis gain variation of the detector cells are removed from the projection data array.

18 Claims, 4 Drawing Sheets

DETECTOR Z-AXIS GAIN NON-UNIFORMITY CORRECTION IN A COMPUTED TOMOGRAPHY SYSTEM

FIELD OF THE INVENTION

This invention relates generally to computed tomography (CT) imaging and more particularly, to correcting image data for any error introduced into such data due to combining the output signals of x-ray detector cells having different individual gains.

BACKGROUND OF THE INVENTION

In at least one known CT system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector. In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

Detectors utilized in CT systems include detectors generally known as 2-D detectors. With such 2-D detectors, a plurality of detector cells form separate columns and the columns are arranged in rows. In a CT system having such a 2-D detector, sometimes referred to as a multislice system, the intensity of detector measurements are derived by combining, along the z direction, multiple detector outputs. These outputs are supplied as inputs to a data acquisition system. If the detector outputs to be combined are obtained from detectors having different individual gains, the combined signal represents a weighted sum of the incoming detector signals where the different detector gains cause different weighting. The error introduced by detector gain differences is object-dependent and cannot be removed by a standard gain calibration.

To more accurately create an image from such data, it is known to estimate the error due to combining the data from x-ray detector cells having different individual gains. One algorithm for estimating the error is described in "DETECTOR Z-AXIS GAIN CORRECTION FOR A CT SYSTEM", U.S. patent application Ser. No. 08/376,813, filed on Jan. 23, 1995, and assigned to the present assignee. Such algorithms are premised on the mathematical assumption that the z-profile of an x-ray beam approximates a rectangular shape. Similarly, such algorithms assume that the norm of detector gain z-profiles is a rectangular shape, and that the detectors do not significantly deviate from the norm.

It is known, however, that the z-profile of an x-ray beam sometimes does not approximate a rectangular shape. Similarly, the norm of detector gain z-profiles does not always approximate a rectangular shape, and thus detectors are known to deviate significantly from the norm.

It would be desirable to more accurately create an image from data regardless of the shape of the x-ray beam x-profile. It also would be desirable to more accurately generate an image regardless of the shape of the detector gain profiles. It further would be desirable to provide such imaging without significantly increasing the cost of the system.

SUMMARY OF THE INVENTION

These and other objects may be attained in a system which, in one embodiment, corrects the error in projection data resulting from the combination of the data from x-ray detector cells having different individual gains. More particularly, the present algorithm estimates the error due to combining the data from x-ray detector cells having different individual gains. The estimated error is subtracted from the projection data thereby removing such error from the projection data.

In accordance with one embodiment of the present invention, actual detector cell gain profiles are used to determine a norm detector cell gain profile. Particularly, the norm detector cell gain profile is determined by locally averaging the detector cell gain profiles. Using local averaging, the norm is non-rectangular, and provides slow channel-to-channel variation between detector cells. Furthermore, the detector cell gains are believed to deviate, if at all, a small amount from the determined norm.

In addition, effective detector cell gain profiles, rather than actual detector cell gain profiles, are used to correct error. Particularly, the z-profile of the x-ray beam across the detector cells and the actual detector cell gain profiles are used to generate effective detector cell gain profiles. The effective detector cell gain profiles are utilized in a correction algorithm to correct the error in projection data resulting from the combination of the data from x-ray detector cells having different individual gains. The effective detector cell gain profiles may be calculated with a non-rectangular x-ray beam, and thus enable error correction in systems using such non-rectangular x-ray beams.

The effective detector cell gain profiles and the determined norm are used in an algorithm to correct for errors. Particularly, and after correcting data from the x-ray detector cells for beam-hardening, the data is passed through a highpass filter to remove any data representing relatively slow, i.e., low frequency, changes. High pass filtering provides an approximate "rough" separation of the error data from the true signal data.

The error data is then clipped and "view averaged" to remove high frequency data contents which are true signal data. Particularly, some actual data from the image to be reconstructed has a high frequency and should be filtered out. Clipping and view averaging removes the high frequency object data while maintaining the error data due to the detector gain variation.

Based on the clipped and "view averaged" estimate, intensity slope estimates along the z-direction are generated.

An error estimate based on such slope estimates is then determined. Such error estimate then is subtracted from the beam-hardening corrected data to remove the error data from the projection data. In this manner, errors due to z-axis gain variation of the detector cells are corrected.

The above described system enables accurate estimation of error due to varying detector cell gain profiles. Furthermore, the system enables correction with non-rectangular shaped x-ray beam profiles. In addition, the system provides a non-rectangular shaped norm of detector cell gain profiles, thus reducing artifacts in a displayed image. The system also does not significantly increase the cost of the imaging system.

DETAILED DESCRIPTION OF THE DRAWINGS

Figure 1:
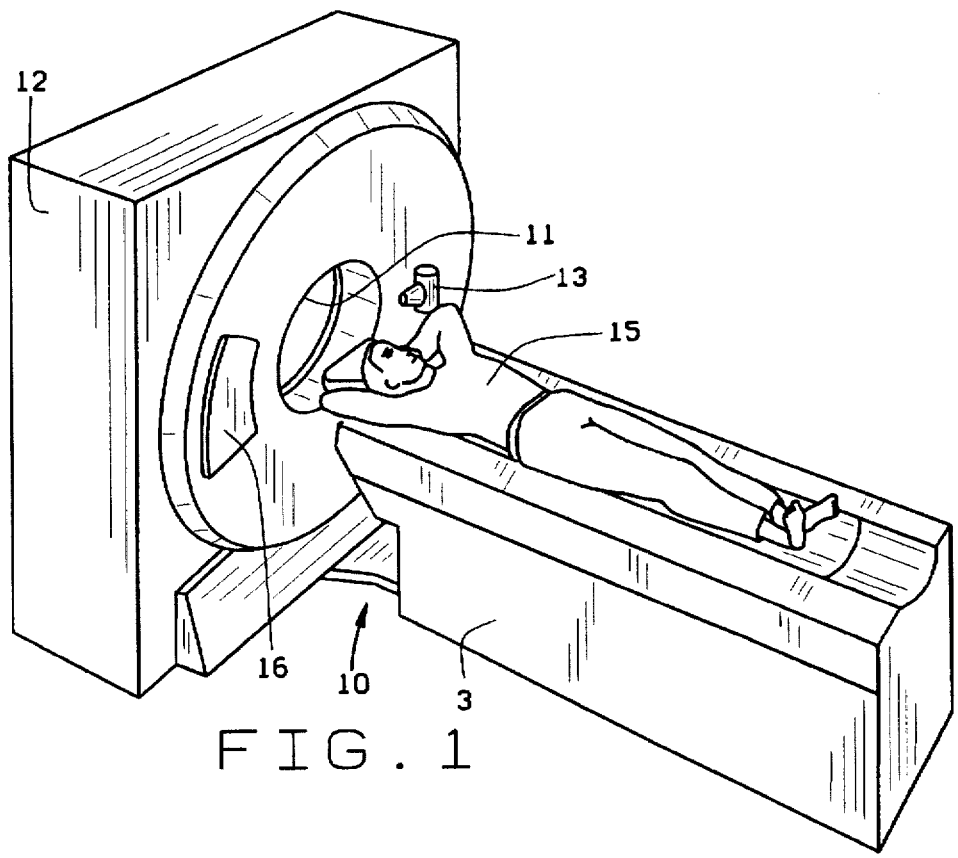
FIG. 1 is a pictorial view of a CT imaging system.
Figure 2:
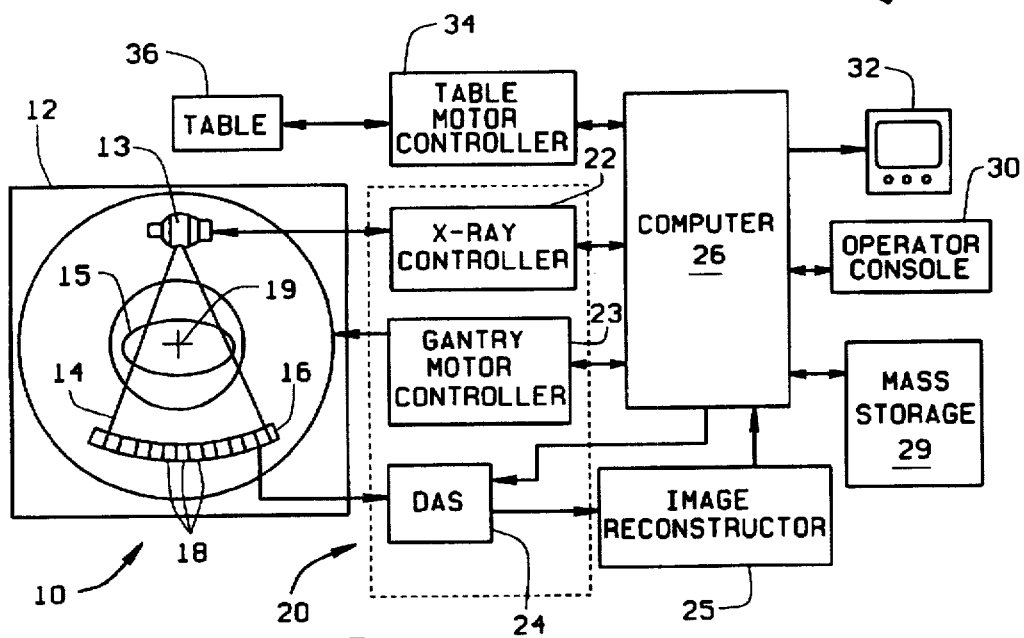
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through a medical patient 22. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

Figure 3:
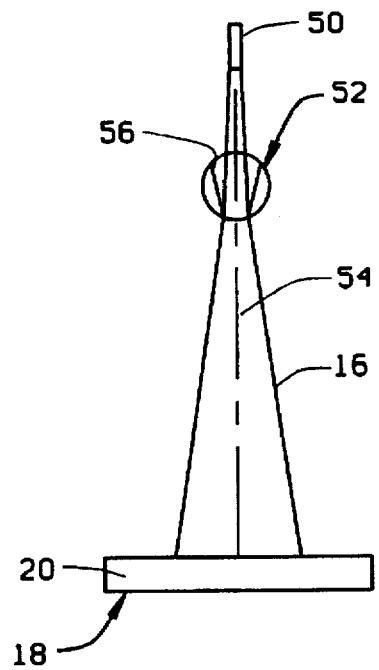
FIG. 3 is a schematic illustration of a beam focal spot, collimator and detector.

Referring to FIG. 3, x-ray beam 16 emanates from a focal spot 50 of source 14 (not shown in FIG. 3). X-ray beam 16 is collimated by a pre-patient collimator 52 and is projected toward detector cell 20 of detector array 18. A plane 54, generally referred to as the "fan beam plane", contains the centerline of focal spot 50 and the centerline of beam 16.

Collimator 52 has a substantially circular cross-sectional shape and an aperture 56 extends through collimator 52. A plurality of other collimator apertures (not shown) may also be formed in and extend through collimator 52, and each aperture corresponds to a particular slice width. For example, aperture 56 may correspond to a 10 mm slice width and another aperture may correspond to a 7 mm slice width. If a scan is to be performed for a 10 mm slice, then aperture 56 is aligned with expected x-ray focal spot 50 and restricts beam 16 projected from focal spot 50 to 10 mm. Collimator 52 is well known in the art.

Figure 4:
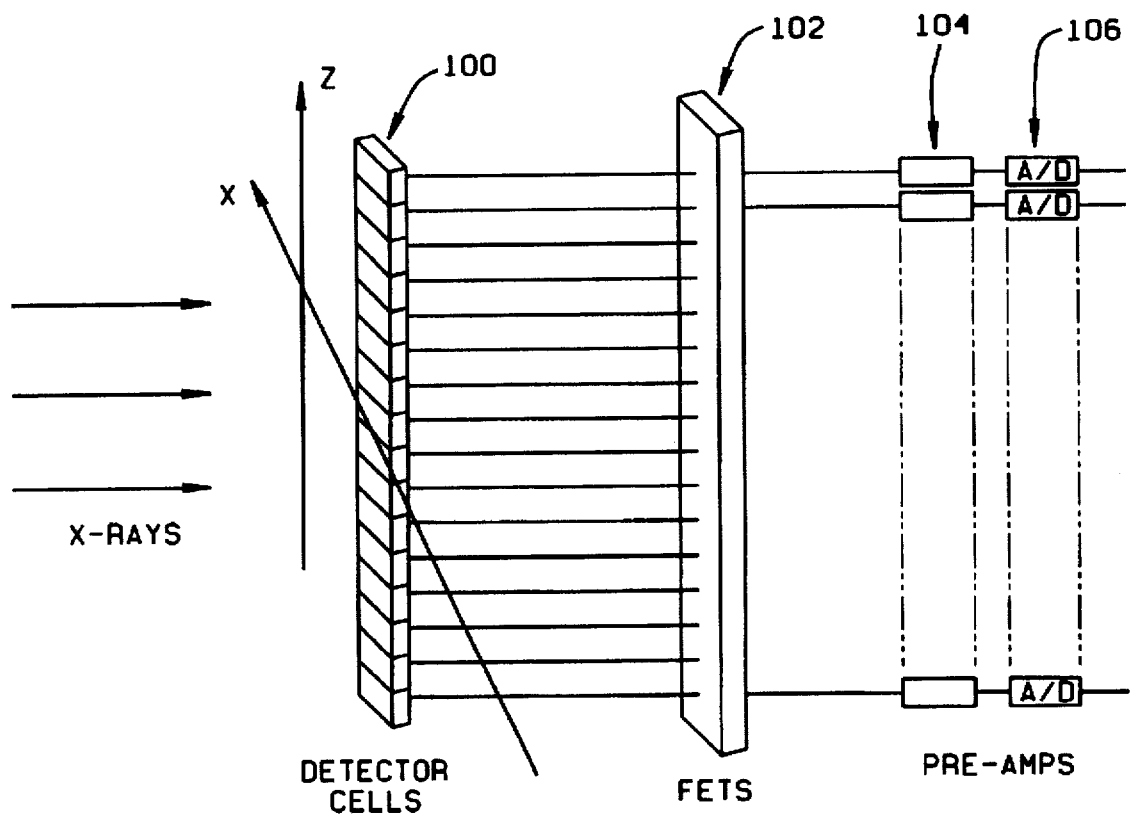
FIG. 4 is a block diagram depiction of a column of detector cells of a detector and related controls.

FIG. 4 illustrates a column of detector cells 100 coupled to switches (e.g. field effect transistors (FETS)) 102. Detector column 100 is composed of a plurality of detector cells arranged in a column. Although not shown, a complete detector is composed of a plurality of detector columns forming rows of detector cells along the z-axis. As explained above, each detector cell produces an electrical signal that represents the intensity of an impinging x-ray beam and hence the attenuation of the beam as it passes through a patient. The output of each cell is supplied through FETs 102 to preamplifiers 104 which supply an amplified signal to an analog-to-digital converters 106. The digitized signal is then supplied to computer 26 for further processing and image reconstruction.

In operation, FETs 102 controls supply of output signals from each detector cell row to the pre-amplifiers 104. For example, FETs 102 are "opened" and "closed" under the control of switch control assembly (not shown). When a particular FET is closed, the output signal from the corresponding detector cell is provided to pre-amp 104. When the FET is open, no signal is provided by such cell to pre-amp 104.

FETs 102 may enable one or more than one detector cell during a particular sample time. For example, one detector cell in a column may be enabled during each sample time. Two cells also may be enabled during each sample time. Pre-amps 104 provide an amplified output of such signals to A/D converters 106.

Figure 5:
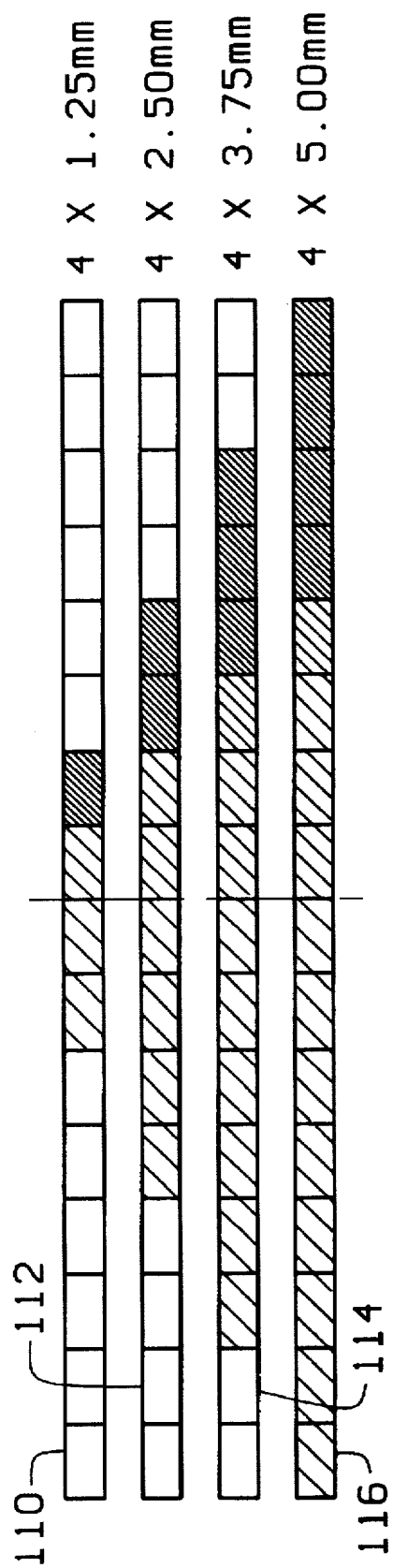
FIG. 5 illustrates detector cell data combining for various thickness image slices.

The number of cells activated in each channel during each sample time is determined by the slice dimensions of the image desired to be reconstructed. For example, as shown in FIG. 5, sixteen detector cells are arranged in a column. Although shown horizontally in FIG. 5, it should be understood that the cells in FIG. 5 correspond to the column shown in FIG. 4. It also should be understood that either more or fewer than sixteen cells may be arranged in a column. The top column 110 corresponds to the cell outputs for an image slice that is 4×1.25 mm in size. The bottom column 116 corresponds to the cell combinations for an image slice that is 4×5.00 mm in size.

With a thin slice (e.g., a 4×1.25 mm slice), no summing of detector cells is performed. For a thicker slice (e.g., a 4×2.50 mm slice), detector cell summing is performed. As shown in FIG. 5, for the 4×2.50 mm slice, two cells are summed as shown in column 2 (112) as indicated by shading. For the 4×3.75 mm slice (column 3 (116)), three cells are summed, and for the 4×5.00 mm slice (column 4 (118)), four cells are summed. Such summing is performed when reconstructing images for thicker slices since for thicker slices, adequate coverage can be obtained and processing time can be reduced by summing the detector cell outputs as set forth above.

When summing detector cell outputs, an error is introduced into the summed signal due to the fact that each detector cell has a different gain. When the detector cell outputs are summed, the error due to the different gains is included in the resulting signal (e.g., the digitized signal output by A/D converter 106).

One known algorithm for correcting the projection data for errors resulting from combining signals from detector cells having different gains is described in "DETECTOR Z-AXIS GAIN CORRECTION FOR A CT SYSTEM", patent application Ser. No. 08/376,813, filed date of Jan. 23, 1995, assigned to the present assignee. Using such algorithm, data provided to computer 36 (FIG. 2) typically first is preprocessed (by computer 36) to correct for various well-known errors such as beam-hardening. The algorithm is then implemented to form a part of such preprocessing after beam-hardening correction but before PCAL correction.

The known algorithm is premised on the assumptions that the z-profile of x-ray beam 16 has a generally rectangular shape, and that the norm of the detector gain z-profiles also has a generally rectangular shape. For example, and assuming that four detectors are combined in the z direction to define a 5 mm slice, the known algorithm operates as follows. The four detectors to be combined have individual gains $g_k$ where k=1, 2, 3, 4. The x-ray intensity seen by each individual detector is $I_k$ where k=1, 2, 3, 4. The measured data, denoted as Y, is modeled as follows:

$$Y = \sum_{k=1}^{k=4} g_k I_k. \quad (1)$$

To normalize the detector gains, the shape of the norm is assumed to be generally rectangular, and the gain-normalized data $I_m$ is given by:

$$I_m = Y/G = \sum_{k=1}^{k=4} (g_k/G) I_k, \quad (2)$$

where G is the average gain of the combined module to be considered, i.e.:

$$G = 1/4 \sum_{k=1}^{k=4} g_k. \quad (3)$$

The measurement desired to be obtained, denoted as $\tilde{I}$, is:

$$\tilde{I} = \sum_{k=1}^{k=4} I_k. \quad (4)$$

The gain of each individual detector is expressed as:

$$g_k = G + \delta g_k, \quad (5)$$

where $\delta g_k$ is the remaining part of $g_k$. The physical meaning of $\delta g_k$ is the gain variation of the detectors. Using equation 5 with equation 2, factorizing G and recalling equation 4 provides:

$$I_m = \sum_{k=1}^{k=4} + \sum_{k=1}^{k=4} I_k(\delta g_k/G) I_k = \tilde{I} + \sum_{k=1}^{k=4} (\delta g_k/G) I_k. \quad (6)$$

Equation 6 relates the true signal, $\tilde{I}$, the signal derived from the measured data, $I_m$, and the error due to the detector z-axis gain variation.

Given that log (1+x)≈x and $I_m \approx \tilde{I}$, equation 6 can be rewritten as follows:

$$-\log(\tilde{I}) = -\log(I_m) + \Delta E, \quad (7a)$$

where $$\Delta E = \sum_{k=1}^{k=4} (\delta g_k/G)(I_k/\tilde{I}). \quad (7b)$$

The algorithm then removes the z-axis error.

However, the above-described algorithm is not particularly effective where (1) the shape of the profile of x-ray beam 16 is non-rectangular, or (2) the shape of the norm of detector gain profiles is non-rectangular. The profile of x-ray beam 16 often is non-rectangular. Particularly, the profile of x-ray beam 16 is non-rectangular when both x-ray umbra and x-ray penumbra are used for imaging. Similarly, the shape of the norm of detector gain profiles is often non-rectangular. In addition, and to assure slow channel-to-channel variation between detectors, it often is desirable for the norm to be non-rectangular. The present algorithm, in one embodiment, corrects projection data acquired with an x-ray beam having a non-rectangular profile. The present algorithm also provides for a non-rectangular norm of detector gain profiles, while simultaneously providing slow channel-to-channel variation between detectors.

In accordance with one embodiment of the present invention, data provided to computer 36 (FIG. 2) typically first is preprocessed (by computer 36) to correct for various well-known errors such as beam-hardening. The present correction algorithm could be implemented to form a part of such preprocessing after beam-hardening correction but before PCAL correction, as illustrated in FIG. 6.

Figure 6:
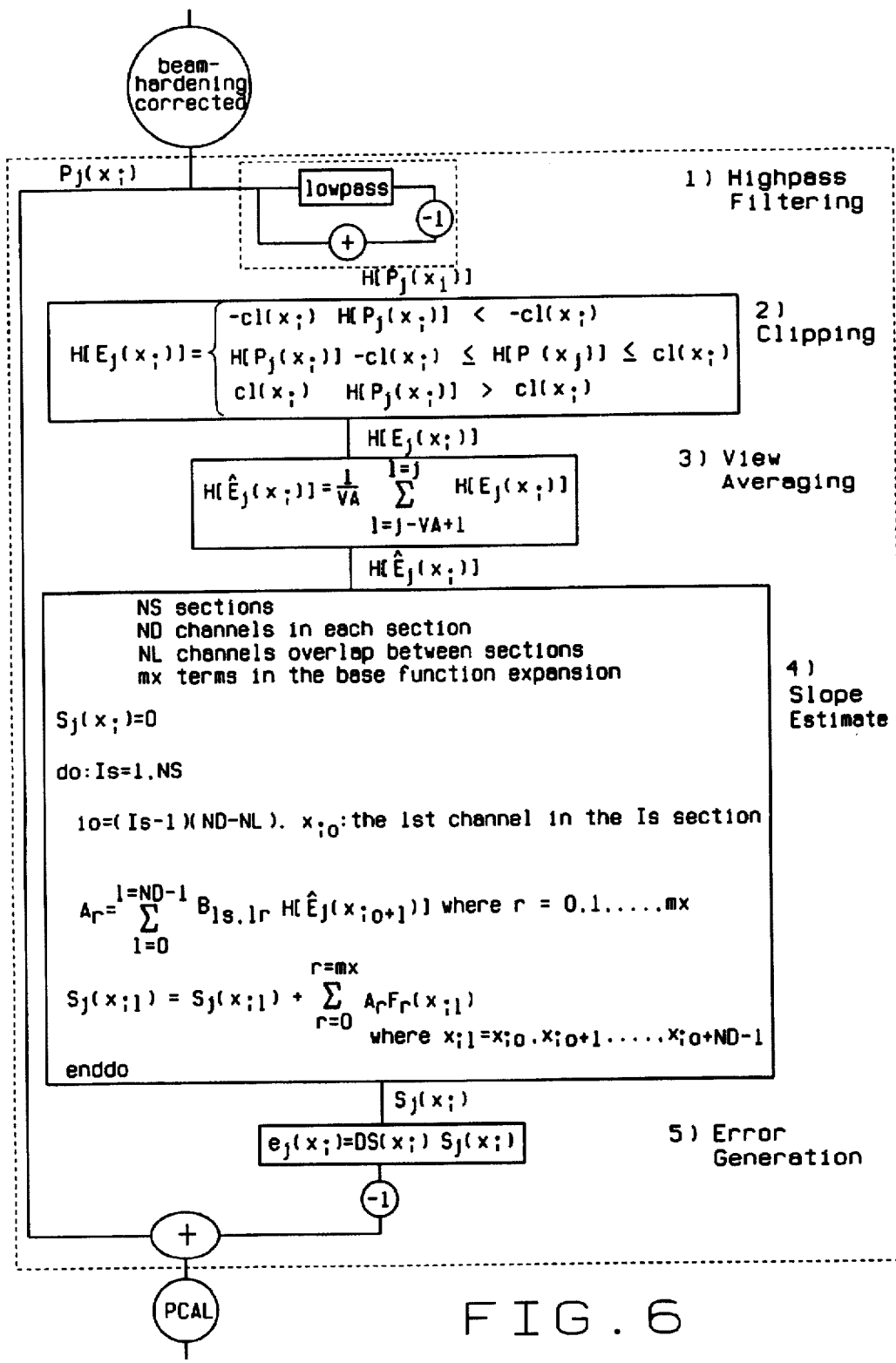
FIG. 6 is a flow chart illustrating a sequence of process steps in accordance with one form of the present invention.

Referring to the flow chart illustrated in FIG. 6, assume that z detectors are combined in the z direction to define a slice. Assume also that x channels of detectors contribute to the image slice. The detectors have actual detector gain profiles g(x,z) where x is the channel index and z is the z location index. Actual detector gain z-profiles g(x,z) are locally averaged (in x) to normalize the detector gain profiles. Particularly, the local average (in x) of the actual detector gain z-profiles g(x,z) defines the norm function of detector gain profiles.

More specifically, assume that an individual detector cell 20 output is defined as $X_j(i,j)$ for a detector cell 20 in ith channel in the lth row of the jth view. After raw data is acquired at such cell, offset correction, reference normalization, channel expansion and view averaging are performed. The resulting detector cell gain for such detector cell is represented by $Xv_j(i)$.

The present correction algorithm corrects for image artifacts resulting from a z-axis slope in projection intensity which is caused by non-uniform patient 22 anatomy interacting with the variation of detector cell to cell gain differences. As described above, a z-axis slope gain calibration is performed to determine individual detector cell gains and generate z-axis slope correction vectors. The x-ray beam profile for the measured cell gains is then corrected to reduce artifacts caused by using a non-uniform x-ray beam profile during such cell gain measurement.

Specifically, a non-uniform x-ray beam profile is estimated using the detector cell gain data. Since x-ray beam profile varies slowly in the x-direction, the x-ray beam profile may be estimated by low-pass filtering the raw detector cell gain data in the x-axis. For example, x-ray beam profile can be estimated by performing multiple point box-car averaging of normalized raw detector gain, where the normalization is performed column by column to the maximum gain value in the column.

As one specific example, the x-ray beam profile is estimated by normalizing raw gain data to a maximum gain value along the z-direction for each channel. The normalized data over ns channels is then averaged in accordance with:

$$bp_l(s) = \frac{1}{ns} \sum_{i=is}^{is+ns} (Xv_l(i)/maxXv_l(i)) \qquad (8a)$$

$$1 \leq l \leq 16$$

where $bp_l(s)$ is the estimated beam and detector profile averaged over ns channels for a detector cell in an lth row and an sth section. To facilitate a smooth transition, box car averaging may be performed, for example, section by section with at least some overlapping channels.

The estimated profile $bp_l(s)$ is then normalized, section by section, to maximum values in accordance with:

$$BP_l(s) = \frac{bp_l(s)}{\max(bp_l(s))} \qquad (8b)$$

$$1 \leq l \leq 16$$

Estimated profile $BP_l(s)$ contains both the x-ray beam profile and an average detector gain profile over ns channels along the x-direction.

Estimated profile $BP_l(s)$ is then utilized to normalize cell gains $Xv_l(i)$ for each local section s in accordance with:

$$Xc_l(i)^W = \frac{Xv_l(i)/maxXv_l(i)}{BP_l(s)^W} \quad W1 \leq l \leq W2 = \frac{Xv_l(i)/maxXv_l(i)}{1 - \delta BP_l(s)^W} \qquad (9a)$$

for $i = ns/4 + s*ns/2, \ldots ns*3/4 + s*ns/2,$ $s = 0, 1, \ldots S$ where $$\delta BP_l(s)^W = \frac{maxbp_l(s) - bp_l(s)}{maxbp_l(s)} = 1 - \frac{bp_l(s)}{maxbp_l(s)}$$

$$W1 \leq l \leq W2 \qquad 1 \leq l \leq 16$$

W is a slice width; and
$Xc_l(i)$ is a normalize cell gain.

Alternatively, estimated profile $BP_l(s)$ may be utilized to normalize cell gains $Xv_l(i)$ for each section s in accordance with:

$$Xc_l(i)^W = Xv_l(i)/maxXv_l(i)(1 + \delta BP_l(s)^W) \qquad (9b)$$

$$1 \leq l \leq 16$$

for $i = ns/4 + s*ns/2, \ldots ns*3/4 + s*ns/2,$ $s = 0, 1, \ldots S$ where $$\delta BP_l(s)^W = \frac{maxbp_l(s) - bp_l(s)}{maxbp_l(s)} = 1 - \frac{bp_l(s)}{maxbp_l(s)}$$

$$W1 \leq l \leq W2 \qquad 1 \leq l \leq 16$$

From equations (9a) and (9b), it is shown that the correction method is correlated by a 1st order Taylor expansion with 2nd and higher order terms neglected. The section number and channel number in a section may be selected, for example, to be optimized based on IQ simulation of z-axis slope correction since they may have the potential to improve the effectiveness of the correction algorithm.

This normalized gain, i.e., $Xc_l(i)^W$ is referred to hereinafter as effective detector gain profile $g_{eff}(x,z)$, and is channel-dependent. In addition, such normalized gain provides for a channel-to-channel variation slow enough to reduce production of artifacts. Furthermore, such local averaging provides for substantially small deviation between actual detector gain z-profiles g(x,z) and the normalized detector gain profile.

As described above, the present algorithm also utilizes the actual detector gain profiles g(x,z) to generate effective detector gain profiles $g_{eff}(x,z)$. The effective detector gain profiles $g_{eff}(x,z)$ are related to the actual detector gain profiles g(x,z) in accordance with the general equation:

$$g_{eff}(x,z) = I_0(x,z) * g(x,z), \qquad (10)$$

where $I_0(x,z)$ denotes the z-profiles of x-ray beam 16 at a detector at channel x and location z.

The shape of the profiles of x-ray beam 16 is determined in accordance with the focal spot 50, the collimator aperture 56, and the geometry of x-ray beam 16. Particularly, the centerline of x-ray beam 16, the width of collimator aperture 56, and the size of focal spot 50 define the z-profiles of x-ray beam 16. The width of collimator aperture 56, the size of focal spot 50 and the location of centerline may be measured before a scan. For example, the location of centerline may be determined by a z-position sensor. Such values also may be approximated using known analytical models. Such values may then be stored, for example in computer 36 for use during a scan. Alternatively, the effective detector gain profiles $g_{eff}(x,z)$ may be directly measured with collimator aperture 56 in accordance with both the umbra and penumbra of x-ray beam 16.

The determined effective detector gain profiles $g_{eff}(x,z)$ are utilized to determine and correct error in projection data. For example, again assume that four detectors in one channel x, are combined in the z-direction to define a slice. The number of detectors combined, of course, may vary and could be less than or greater than 4 (e.g., the number of detectors combined could be generally represented by the designation "nz"). Each detector has an effective gain profile $g_{eff_k}$ where k=1, 2, 3, 4. The x-ray intensity seen by each individual detector is $I_k$ where k=1, 2, 3, 4. The measured data, denoted as Y, is modeled as follows:

$$Y = \sum_{k=1}^{k=4} g_{eff_k} I_k. \qquad (11)$$

The gain-normalized data $I_m$ is given by:

$$I_m = Y/G = \sum_{k=1}^{k=4} (g_{eff_k}/G) I_k, \qquad (12)$$

where G is the average gain of the combined module to be considered, i.e.:

$$G = 1/4 \sum_{k=1}^{k=4} g_{eff_k}. \qquad (13)$$

The measurement desired to be obtained, denoted as $\tilde{I}$, is:

$$\tilde{I} = \sum_{k=1}^{k=4} I_k. \qquad (14)$$

The gain of each individual detector is expressed as:

$$g_{eff_k} = G + \delta g_{eff_k}, \qquad (15)$$

where $\delta g_{eff_k}$ is the remaining part of $g_{eff_k}$. The physical meaning of $\delta g_{eff_k}$ is the gain variation of the detectors. Using equation 15 with equation 12, factorizing G and recalling equation 14 provides:

$$I_m = \sum_{k=1}^{k=4} I_k + \sum_{k=1}^{k=4} I_k(\delta g_{\mathit{eff}_k}/G)I_k = \tilde{I} + \sum_{k=1}^{k=4} (\delta g_{\mathit{eff}_k}/G)I_k. \quad (16)$$

Equation 16 relates the true signal, I, the signal derived from the measured data, $I_m$, and the error due to the detector z-axis gain variation.

Given that $\log(1+x) \approx x$ and $I_m \approx I$, equation 14 can be rewritten as follows:

$$-\log(I) \approx -\log(I_m) + \Delta E, \quad (17a)$$

where $$\Delta E = \sum_{k=1}^{k=4} (\delta g_{\mathit{eff}_k}/G)(I_k/\tilde{I}). \quad (17b)$$

If the z profile of the incoming x-ray flux $I_k$ is known, equations 17a and 17b can be used to remove the x-axis error. Estimating $I_k$ adequately is important in accurately removing such error.

Equation 17b holds for every data point. Thus, there are a total of (Nx×Nz) equations, where Nx and Nz represent the number of data samples per view along the fan beam direction (the x direction) and along the direction perpendicular to the fan beam (the z direction), respectively. Although all these equations can be used simultaneously, in accordance with one form of the present algorithm, only the data from the same detector row (the same z location) are coupled to solve the simultaneous equations. Particularly, i denotes the x index (the channel Index), where i=1, 2, . . . n. This results in n equations:

$$\Delta E(x_i) = \sum_{k=1}^{} ((\delta g_{\mathit{eff}}(x_i,z_k)/G(x_i))(I(x_i,z_i)/\tilde{I}(x_i)) \quad (18)$$

where $i = 1, \ldots, n$

An accurate and stable solution can be achieved by a high pass version of equation 18. A linear highpass operator, $H[f(x)]$, can be defined as:

$$H[f(x)] = f(x) - \text{Lowpass}[f(x)], \quad (19)$$

where Lowpass $[f(x)]$ is a low-passed version of $f(x)$. As an example, several points boxcar average can be used. Applying this operator to equation 18 provides:

$$H = [\Delta E(x_i)] = \sum_{k=1}^{k=4} H[(\delta g(x_p,z_i)/G(x_i))][I(x_p,z_i)/\tilde{I}(x_i)], \quad (20)$$

where $i = 1, \ldots, n$

In equation 20, it is assumed that the part of $I(x_i,z_k)/\tilde{I}(x_i)$ that causes the z-axis problem changes relatively slowly in the x direction, and therefore, can be factored out from the highpass operator. Equation 20 provides a mathematical foundation for matching the detector "finger prints", as defined by the high-passed gains, with the error term.

Over a certain region, $I(x_i,z_k)/\tilde{I}(x_i)$ can be further approximated by some low-frequency base functions. As an example, the following is provided by using a power series expansion:

$$I(x,z)/\tilde{I}(x) = \sum_{iz=1}^{iz=mz} c_{iz}(x)z^{iz} = c_1(x)z. \quad (21)$$

The $c_0(x_i)$ term has no contribution to the z-axis correction, and therefore, is ignored. Also, only the linear term with respect to z is retained in the second part of equation 21. Under the assumption of a slope term only in z, equation 20 can be rewritten as:

$$H[\Delta E(x_i)] = H[(3(g_{\mathit{eff}_4}(x_i)-g_{\mathit{eff}_1}(x_i))+(g_{\mathit{eff}_3}(x_i)-g_{\mathit{eff}_2}(x_i)))/G(x_i)] \\ c_1(x_i)\Delta z. \quad (22)$$

Since the error term depends only on gain variations, an erroneous slope estimate does not contribute an error term to those channels which have no gain variations.

The function $c_i(x_i)$ can be further expanded as follows:

$$c_1(x) = \sum_{ix=0}^{ix=mx} c_{ix}x^{ix}. \quad (23)$$

The corresponding coefficients can be determined by solving equations 20 or 22 in the least squares sense.

Although in equation 20 or 22 $H[\Delta E(x)]$ is unknown, it can be estimated. As an example, a value can be approximated by the corresponding highpass version of the projection data $P(x_i)$, i.e., $H[\Delta E(x)] \approx H[P(x)]$, as suggested by equation 17a. $H[P(x)]$ not only contains the errors due to the detector gain variation, but also contains high frequencies that belong to the object being imaged. To obtain robust and stable corrections, an estimation of $H[\Delta E(x)]$ that minimizes the high frequency contents from the object while maintaining the errors due to the detector gain variation should be used.

The following two techniques can be used to improve the $H[\Delta E(x)]$ estimation:

1) $c_M$ denotes the maximal value of $c_i(x_i)$ in clinical applications. It then follows from equations 20 and 21 that:

$$|H[\Delta E(x_i)]| \leq c_M f(x_i) \quad (24a)$$

$i = 1, \ldots, n$ $$\text{where } f(x_i) = \left| \sum_{k=1}^{k=4} H[\delta g(x_p,z_k)/G(x_i)]z_k \right|. \quad (24b)$$

$f(x_i)$ is a function of the detector gain characteristics only and can be precalculated. Thus, the $H[\Delta E(x)]$ estimation that does not satisfy equation 24a can be clipped as follows:

$$H[\Delta E(x_i)] = \begin{cases} -c_M f(x_i) & H[P(x_i)] < -c_M f(x_i) \\ H[P(x_i)] & -c_M f(x_i) \leq H[P(x_i)] \leq c_M f(x_i) \\ c_M f(x_i) & H[P(x_i)] > c_M f(x_i) \end{cases} \quad (25)$$

2) The $H[\Delta E(x)]$ estimation derived from equation 25 can be averaged across views to further suppress the high frequency contents that belong to the object being imaged.

With the improved estimation of $H[\Delta E(x)]$, the corresponding coefficients in equation 23 can be determined in the least squares sense. The base function expansion works well for fitting a small region. When the fitting region is large, it can be subdivided into sub-regions and fitted separately. Some feathering can be applied to assure a smooth transition between sub-regions.

The closeness of this fitting can be evaluated by computing the correlation coefficients, denoted as r. h(r) denotes the closeness index, where $0 \leq h(r) \leq 1$. The higher the value of h(r), the closer the fitting. Thus, the final estimate of $I(x_i,z_k)/\tilde{I}(x_i)$ can be expressed in one of the following ways:

$$I(x,z)/\tilde{I}(x) \approx z \sum_{ix=0}^{ix=mx} c_{ix} x^{ix}, \quad (26a)$$

$$I(x,z)/\tilde{I}(x) \approx h(r)z \sum_{ix=0}^{ix=mx} c_{ix} x^{ix}, \quad (26b)$$

$$I(x,z)/\tilde{I}(x) \approx h(r)z \sum_{ix=0}^{ix=mx} c_{ix} x^{ix} + (1-(h(r))zS. \quad (26c)$$

where S is an estimate of $I(x_i,z_k)/\tilde{I}(x_i)$ derived by other known methods. Once the function $I(x_i,z_k)/\tilde{I}(x_i)$ is determined, equations 17a and 17b can be used to remove the z-axis error.

To reduce the implementation burden, it might be sufficient to update the $I(x_i,z_k)/\tilde{I}(x_i)$ estimation once every several views. The interval for updating the stimulation can be determined by experiment.

Referring now specifically to FIG. 6, one form of the present correction algorithm is outlined in the dashed box 150. As set forth in FIG. 6, the algorithm can be applied after beam hardening correction 152 but before the PCAL correction 154 and includes the following five steps: 1) highpass filtering, 2) clipping, 3) view averaging, 4) slope estimate, and 5) error generation. In FIG. 6, the j and i indexes represent the view and channel indexes.

The first step of high pass filtering is described in equation 19. The second step of clipping is described in equation 25, where the ceiling function $cl(x_i)$ is described in equation 24a. View averaging is shown as the third step in FIG. 6.

The fourth step of generating a slope estimate is an important step in the present algorithm. The NC center channels where the correction is to be applied are subdivided into NS sections, with ND channels in each section and NL channels overlap between adjacent sections. The slope is estimated section by section. $x_{i0}$ denotes the first channel in the Isth section. mx+I is the number of terms retained in equation 21. For the Isth section, a (mx+1)×ND matrix, $(b_{is,r,l})$, is defined as follows:

$$b_{is,r,l} = f(x_{i0+l})(l - 0.5ND)^r \quad (27a)$$

for $l = 0, \ldots, ND - 1$ and $r = 0, \ldots, mx$ $$\text{where } f(x) = \sum_{k=1}^{k=nz} H[\delta g(x,z_k)/G(x)]z_k. \quad (27b)$$

$(B_{is,l,r})$ denotes the inverse matrix of $(b_{is,r,l})$. $(B_{is,l,r})$ is a ND×(mx+1) matrix. Furthermore, functions $F_r(x_{10+l})$ are defined as follows:

$$F_r(x_l) = K(x_l - x_o)(l - 0.5ND)^r \quad (28)$$

for $l = 0, \ldots, ND - 1$ and $r = 0, \ldots, mx$ where, $K(x_1-x_0)$ is a feathering function to assure a smooth transition from section to section. An example of the feathering function is given as follows:

$$K(x) = \begin{cases} 0 & x \leq 0 \\ 3(x/NL)^2 - 2(x/NL)^3 & 0 < x < NL \\ 1 & NL \leq x \leq ND - NL \\ 3(ND - x/NL)^2 - 2(ND - x/NL)^3 & ND - NL < x < ND - 1 \\ 0 & x \geq ND - 1 \end{cases} \quad (29)$$

With $(B_{is,l,r})$ and $F_r(x_l)$ defined as above, the fourth step can be carried out as illustrated in FIG. 6.

The detector Z-slope sensitivity function, DS(s), is defined as follows:

$$Ds(x) = \sum_{k=1}^{k=nz} (\delta g(x,z_k)/G(x))z_k. \quad (30)$$

Therefore, the fifth step of error generation can be performed as shown in FIG. 6.

The ceiling function $cl(x_i)$, the slope estimate matrix $(B_{is,l,r})$ and the detector Z-slope sensitivity $DS(x_i)$ depend on detector characteristic and the slice thickness only, and therefore can be pre-calculated during the detector gain determination. $F_r(x_i)$ is determined by the parameters ND and NL and mx, and can also be pre-calculated.

Example parameters of the algorithm illustrated in FIG. 6 are listed below.

NC: Number of channels to be corrected (650);

NS: Number of sections (14);

ND: Number of channels in each section (60);

NL: Number of overlapping channels between sections (15);

mx and mz: Number of terms in the base function expansion (5,1);

VA: Number of views to be averaged (0,15);

NV: Number of views between two adjacent error updates (0);

FS: Hp filter size (3);

$C_M$: Factor for the ceiling function.

The correction algorithm described above may be used with a plurality of detector cells in the z-direction. For example, the above-described algorithm may be implemented with a twin slice CT system, i.e., with a system having two rows of detector cells in the z-direction. Similarly, such algorithm may be implemented with a single slice CT system. Alternatively, such algorithm may be implemented in multislice CT systems having more than two rows of detector cells in the z-direction.

From the preceding description of several embodiments of the present invention, it is evident that the objects of the invention are attained. Although the invention has been described and illustrated in detail, it is to be clearly understood that the same is intended by way of illustration and example only and is not to be taken by way of limitation. For example, the CT system described herein is a "third generation" system in which both the x-ray source and detector rotate with the gantry. The present invention, however, may be used with many other CT systems including "fourth generation" systems wherein the detector is a full-ring stationary detector and only the x-ray source rotates with the gantry. The present invention could also be utilized in connection with stop-and-shoot as well as helical scanning type CT systems. In addition, the correction algorithm described herein may be used in connection with both single slice and multislice CT systems. Moreover, although the present invention, in one form, has been described being performed on data subsequent to beam-hardening correction, the present invention could be implemented at various points in the data correction/processing. Accordingly, the spirit and scope of the invention are to be limited only by the terms of the appended claims.

What is claimed is:

1. A method for correcting projection data for detector cell gain error in a computed tomography system, the system including an x-ray source for projecting an x-ray beam towards a detector, the detector including a plurality of detector cells, the projection data being generated from output signals from the detector cells, said method comprising:

determining actual detector gain profiles;

determining effective detector gain profiles; and determining error in projection data using the determined actual detector gain profiles and the determined effective detector gain profiles.

2. A method in accordance with claim 1 further comprising the step of determining a norm detector gain profile.

3. A method in accordance with claim 2 wherein determining a norm detector gain profile comprises obtaining a local average of the determined actual detector gain z-profiles.

4. A method in accordance with claim 1 wherein determining effective detector gain profiles comprises the step of determining a z-profile of the x-ray beam.

5. A method in accordance with claim 4 wherein determining effective detector gain profiles comprises the step of multiplying the determined z-profile of the x-ray beam and the determined actual detector gain profiles.

6. A method in accordance with claim 4 wherein the x-ray source includes a focal spot and a collimator, and wherein determining the z-profile of the x-ray beam includes the steps of:

determining a width of the collimator aperture;

determining a focal spot size; and determining a fan beam geometry.

7. A method in accordance with claim 1 wherein determining error in projection data includes the steps of:

high pass filtering the data;

clipping the high-passed filtered data;

view averaging the clipped data;

creating a slope estimate based on the view-averaged data; and identifying the error data using the slope estimate.

8. A method in accordance with claim 1 wherein the computed tomography system is a single slice system.

9. A method in accordance with claim 1 wherein the computed tomography system is a multislice system.

10. A system for producing a tomographic image of an object from projection data, said system comprising an x-ray source and a detector, said detector having a plurality of detector cells, said system correcting the projection data obtained from said detector cells for any error resulting from different individual gains of said cells and configured to:

determine actual detector gain profiles;

determine effective detector gain profiles; and determine error in projection data using the determined actual detector gain profiles and the determined effective detector gain profiles.

11. A system in accordance with claim 10 further configured to determine a norm detector gain profile.

12. A system in accordance with claim 11 wherein to determine the norm detector gain profile, said system is configured to obtain a local average of the determined actual detector gain z-profiles.

13. A system in accordance with claim 10 wherein to determine effective detector gain profiles, said system is configured to determine a z-profile of the x-ray beam.

14. A system in accordance with claim 13 wherein to determine effective detector gain profiles, said system is configured to multiply the determined z-profile of the x-ray beam and the determined actual detector gain profiles.

15. A system in accordance with claim 13 further comprising a focal spot and a collimator having an aperture therein, and wherein to determine the z-profile of the x-ray beam, said system is further configured to:

determine a width of said collimator aperture;

determine a focal spot size; and determine a fan beam geometry.

16. A system in accordance with claim 15 further comprising a computer having a memory, and wherein at least the determined width of the collimator aperture is stored in said computer memory.

17. A system in accordance with claim 10 wherein said detector comprises at least one row of detector cells in a z-direction.

18. A system in accordance with claim 17 wherein said detector comprises at least two rows of detector cells in the z-direction.

* * * * *